(12) United States Patent
Higashi et al.

(10) Patent No.: US 10,761,102 B2
(45) Date of Patent: Sep. 1, 2020

(54) METHOD FOR DERIVATIZING AN S-CIS-DIENE COMPOUND, DERIVATIZATION REAGENT KIT, AND METHOD FOR ANALYZING AN S-CIS-DIENE COMPOUND

(71) Applicants: Tokyo University of Science, Tokyo (JP); National University Corporation Chiba University, Chiba-shi, Chiba (JP); JEOL Ltd., Tokyo (JP)

(72) Inventors: Tatsuya Higashi, Kashiwa (JP); Shoujiro Ogawa, Kashiwa (JP); Fumio Nomura, Chiba (JP); Mamoru Satoh, Chiba (JP); Masaki Takiwaki, Chiba (JP)

(73) Assignees: Tokyo University of Science, Tokyo (JP); National University Corporation Chiba University, Chiba (JP); JEOL Ltd., Tokyo (JP)

(*) Notice: Subject to any disclaimer, the term of this patent is extended or adjusted under 35 U.S.C. 154(b) by 40 days.

(21) Appl. No.: 15/718,809

(22) Filed: Sep. 28, 2017

(65) Prior Publication Data

US 2018/0088137 A1    Mar. 29, 2018

(30) Foreign Application Priority Data

Sep. 29, 2016    (JP) .................................. 2016-190684

(51) Int. Cl.
| | | |
|---|---|---|
| *G01N 33/82* | (2006.01) | |
| *G01N 30/06* | (2006.01) | |
| *G01N 33/58* | (2006.01) | |

(52) U.S. Cl.
CPC ............. *G01N 33/82* (2013.01); *G01N 30/06* (2013.01); *G01N 33/58* (2013.01); *G01N 2030/067* (2013.01)

(58) Field of Classification Search
CPC .... G01N 33/82; G01N 33/58; G01N 30/7266; G01N 30/06; G01N 2030/067; H01J 49/165; H01J 49/0404; H01J 49/0445
See application file for complete search history.

(56) References Cited

U.S. PATENT DOCUMENTS

| | | |
|---|---|---|
| 2013/0137185 A1 | 5/2013 | Holmquist et al. |
| 2016/0061848 A1 | 3/2016 | Holmquist et al. |
| 2017/0261523 A1 | 9/2017 | Holmquist et al. |
| 2018/0088137 A1 | 3/2018 | Higashi et al. |

FOREIGN PATENT DOCUMENTS

| | | |
|---|---|---|
| JP | 2015166740 A | 9/2015 |
| WO | 2011072152 A1 | 6/2011 |

OTHER PUBLICATIONS

Waters Co. "Solvents and Caveats for LC/MS" archived by the Internet Archive Wayback Machine on Jun. 24, 2013, obtained by the examiner at <http://web.archive.org/web/20130624072312/http://www.waters.com/waters/en_US/Solvents-and-Caveats-for-LC-MS/nav.htm?cid=10091173&locale=en_US> on Mar. 29, 2019. (Year: 2013).*
U.S. Appl. No. 15/813,542, A1, Higashi et al., This U.S. patent application has not yet published.
Extended European Search Report for application No. 17193756.8 dated Jan. 11, 2018.
Ogawa et al., "Comparative evaluation of new Cookson-type reagents for LC/ESI-MS/MS assay of 25-hydroxyvitamin D3 in neonatal blood samples", Biomedical Chromatography, Jun. 1, 2016, vol. 30, No. 6, pp. 938-945, GB.
Ding et al., "Quantitative determination of vitamin D metabolites in plasma using UHPLC-MS/MS", Analytical and Bioanalytical Chemistry, Jul. 14, 2010, vol. 398, No. 2, pp. 779-789.
Tatsuya et al., "A specific LC/ESI-MS/MS method for determination of 25-hydroxyvitamin D3 in neonatal dried blood spots containing a potential interfering metabolite, 3-epi-25-hydroxyvitamin D3", Journal of Separation Science, Apr. 1, 2011, vol. 34, No. 7, pp. 725-732.
Ogawa et al., "Analysis of urinary vitamin D3 metabolites by liquid chromatography/tandem mass spectrometry with ESI-enhancing and stable isotope-coded derivatization", Analytical and Bioanalytical Chemistry, Aug. 29, 2014, vol. 406, No. 26, pp. 6647-6654.
Ogawa et al., "Enhancing analysis throughput, sensitivity and specificity in LC/ESI-MS/MS assay of plasma 25-hydroxyvitamin D3 by derivation with triplex 4-(4-dimethylaminophenyl)-1, 2, 4-triazoline-5, 5-dione (DAPTAD) isotopologues", Journal of Pharmaceutical and Biomedical Analysis, Nov. 17, 2016, vol. 136, No. 17, pp. 126-133.
Ogawa et al., "A novel Cookson-type reagent for enhancing sensitivity and specificity in assessment of infant vitamin D status using liquid chromatography/tandem mass spectrometry", Rapid Commun. Mass Spectrom., 2013, pp. 2453-2460, 27.
Office Action issued in JP2016-190684 dated May 12, 2020.
Higashi et al., "A Method for Simultaneous Determination of 25-Hydroxyvitamin D3 and Its 3-Sulfate in Newborn PLasma by LC/ESI-MS/MS after Derivatization with a Proton-Affinitive Cookson-Type Reagent", Mass Spectrometry (Tokyo), 2016, 5(2).
Office Action issued in U.S. Appl. No. 15/813,542 dated Apr. 16, 2020.

* cited by examiner

*Primary Examiner* — Christopher Adam Hixson
(74) *Attorney, Agent, or Firm* — The Webb Law Firm

(57) ABSTRACT

Provided is a method for derivatizing an s-cis-diene compound with a Cookson-type derivatization reagent, the method including adding, in a reaction stopping step of stopping a derivatization reaction of the s-cis-diene compound, a decomposition inhibitor to inhibit decomposition of a derivative to be obtained.

5 Claims, 6 Drawing Sheets

METHOD FOR DERIVATIZING AN S-CIS-DIENE COMPOUND, DERIVATIZATION REAGENT KIT, AND METHOD FOR ANALYZING AN S-CIS-DIENE COMPOUND

Japanese Patent Application No. 2016-190684, filed on Sep. 29, 2016, is hereby incorporated by reference in its entirety.

BACKGROUND OF THE INVENTION

The present invention relates to a method for derivatizing an s-cis-diene compound, a derivatization reagent kit, and a method for analyzing an s-cis-diene compound.

Analysis with a mass spectrometer (hereinafter sometimes referred to as "MS") is known, for example, in a clinical examination at a hospital. In particular, analysis of a substance derived from a biological body, for example, a hormone with a liquid chromatography mass spectrometer (hereinafter sometimes referred to as "LC/MS"), which involves separating a compound by high performance liquid chromatography (HPLC) and ionizing and analyzing the separated substance with the MS, has high sensitivity and specificity as compared to immunoassay and the like that have hitherto been used. Further, the above-mentioned analysis is capable of performing simultaneous analysis of a number of items. Therefore, the above-mentioned analysis is rapidly becoming used widely in recent years. In quantitative analysis, particularly, with an LC/MS/MS using a tandem mass spectrometer (hereinafter sometimes referred to as "MS/MS"), a plurality of substances can be selectively subjected to quantitative analysis with a selected reaction monitoring (hereinafter sometimes referred to as "SRM") mode having sensitivity higher than that of LC/MS.

In recent years, as one example of the analysis of a substance derived from a biological body with LC/MS/MS, analysis of vitamin D (hereinafter sometimes referred to as "V.D.") and vitamin D metabolites in the blood is drawing attention. Vitamin D, which is an s-cis-diene compound, and is a fat-soluble vitamin necessary for regulating calcium metabolism, has an action of increasing the concentration of calcium ($Ca^{2+}$) in the blood as activated vitamin D ($1\alpha,25$-dihydroxyvitamin D, hereinafter sometimes referred to as "$1,25(OH)_2D$"). In addition to the above-mentioned action, in vivo metabolites such as $1,25(OH)_2D$ and 25-hydroxyvitamin D (hereinafter sometimes referred to as "$25(OH)D$") play important roles in controlling expression of proteins involved in differentiation and growth of cells, production and secretion of a hormone, an immune reaction, and the like. Therefore, vitamin D is classified as a hormone in some cases from the viewpoints of the action mechanism and the function.

As described above, vitamin D and vitamin D metabolites (hereinafter sometimes collectively referred to as "vitamin D") have bioactivity in a wide range as well as roles as nutrients, and the excess or deficiency of vitamin D is considered to increase the morbidity of various diseases. Therefore, the number of cases of measurement of vitamin D in the blood is increasing and the analysis of vitamin D with LC/MS/MS makes it possible to accurately analyze individual substances having different activities with satisfactory sensitivity than before.

An atmospheric pressure chemical ionization (APCI) method and an electrospray ionization (ESI) method, and the like are used as an ionization method used in LC/MS/MS. The ESI is an ionization method that is most generally used in LC/MS/MS by virtue of the smallest risk of causing fragmentation, a wide range of applicable compounds, and high operability. However, in general, the ESI responsiveness of V.D. metabolites and content of it in the blood is low, the sensitivity may be insufficient even if LC/MS/MS is used for analysis. In view of the foregoing, in order to enhance the detection sensitivity in LC/MS/MS by increasing the ionization efficiency of the vitamin D metabolites, for example, the vitamin D metabolites are analyzed in some cases after being derivatized with 4-phenyl-1,2,4-triazoline-3,5-dione (PTAD) that is one of Cookson-type derivatization reagents (see, for example, Japanese Patent Application Publication No. 2015-166740). Derivatization of vitamin D with PTAD improves the sensitivity is compared to before derivatization, and enables to perform highly selective detection.

However, further improvement in sensitivity is desired in order to measure a small amount of a sample, for example, blood collected from a newborn baby. For this reason, the inventors of the present invention have developed, as a novel Cookson-type derivatization reagent, 4-(4'-dimethylaminophenyl)-1,2,4-triazoline-3,5-dione (DAPTAD) (see, for example, S. Ogawa, et al., Rapid Commun. Mass Spectrom., 25, 2453-2460 (2013)). Vitamin D derivatized with DAPTAD has signal intensity increased by about 100 times that before derivatization, and the derivatization with DAPTAD is suitable for analyzing a small amount of a sample with LC/MS/MS. The signal intensity obtained by the derivatization with DAPTAD is about 10 times that obtained by the derivatization with PTAD that has hitherto been used. Further, derivatizing 25(OH)D, which is one of the vitamin D metabolites with DAPTAD enables to distinguish and quantitate structural isomers such as 3-epimer (3-epi-25(OH)D), which are inactive interference metabolites, and the selectivity is improved than before.

As described above, the derivatization with DAPTAD is suitable for analysis of vitamin D with LC/MS/MS. However, the inventors of the present invention have found that DAPTAD-derivatives of the vitamin D metabolites are partially decomposed during derivatization in some cases due to the influence of an oxidant and the like used for synthesizing DAPTAD. A decomposition product of DAPTAD-derivative of a certain vitamin D metabolite has the same structure as that of a DAPTAD-derivative of another endogenous vitamin D metabolite. Therefore, the decomposition of derivative makes it difficult to perform accurate quantitative analysis of the vitamin D metabolite.

SUMMARY

According to embodiments of the present invention, there can be provided a method for derivatizing an s-cis-diene compound in which the decomposition of a derivative obtained by derivatization is suppressed, and a derivatization reagent kit.

Further, according to one embodiment of the present invention, there can be provided a method for analyzing an s-cis-diene compound capable of performing accurate quantitative analysis.

According to a first aspect of the present invention, there is provided a method for derivatizing an s-cis-diene compound with a Cookson-type derivatization reagent, the method including adding, in a reaction stopping step of stopping a derivatization reaction of the s-cis-diene compound, a decomposition inhibitor to inhibit decomposition of a derivative to be obtained.

According to a second aspect of the present invention, there is provided a derivatization reagent kit to derivatize an s-cis-diene compound with a Cookson-type derivatization reagent, the derivatization reagent kit including: a Cookson-type derivatization reagent; a reaction stopping agent to stop a derivatization reaction of the s-cis-diene compound; and a decomposition inhibitor to inhibit decomposition of a derivative to be obtained.

According to a third aspect of the present invention, there is provided a method for analyzing an s-cis-diene compound, including analyzing a derivative obtained by the above-mentioned method with a mass spectrometer.

Figure 1:
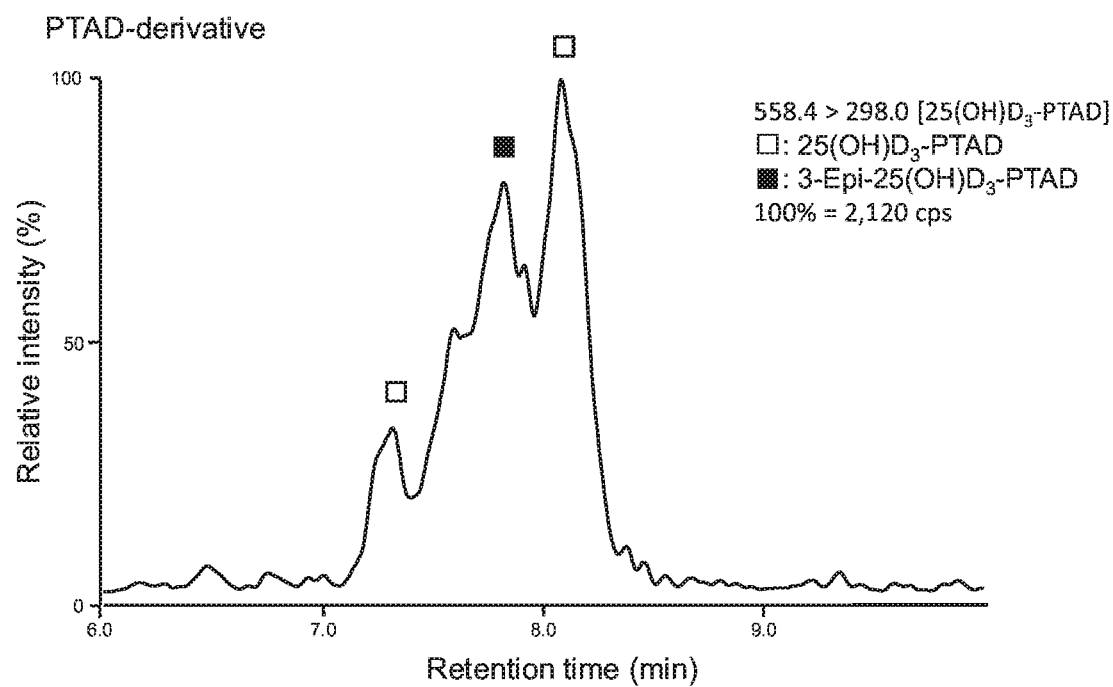
FIG. 1 is a mass chromatogram of $25(OH)D_3$ and 3-epi-$25(OH)D_3$ derivatized with PTAD.

DETAILED DESCRIPTION OF THE EMBODIMENT (1) According to one embodiment of the present invention, there is provided a method for derivatizing an s-cis-diene compound with a Cookson-type derivatization reagent, the method including adding, in a reaction stopping step of stopping a derivatization reaction of the s-cis-diene compound, a decomposition inhibitor to inhibit decomposition of a derivative to be obtained.

In the above-mentioned method, an oxidant remaining in a small amount after being used for producing the Cookson-type derivatization reagent is decomposed by adding the decomposition inhibitor to inhibit the decomposition of the derivative obtained by derivatizing the s-cis-diene compound in the reaction stopping step of stopping the derivatization reaction. Therefore, the decomposition of the derivative to be obtained can be suppressed.

(2) In the above-mentioned method, the Cookson-type derivatization reagent may be 4-(4'-dimethylaminophenyl)-1,2,4-triazoline-3,5-dione (DAPTAD).

In the above-mentioned method, the decomposition of the DAPTAD-derivative to be obtained can be suppressed.

(3) In the above-mentioned method, the s-cis-diene compound may be a steroid.

In the above-mentioned method, the decomposition of the derivative to be obtained can be suppressed.

(4) In the above-mentioned method, the s-cis-diene compound may be vitamin D or a vitamin D metabolite.

In the above-mentioned method, the decomposition of the derivative to be obtained can be suppressed.

(5) In the above-mentioned method, the decomposition inhibitor may be ammonia or an amine.

In the above-mentioned method, the decomposition of the derivative to be obtained can be suppressed with ammonia or the amine as the decomposition inhibitor.

(6) In the above-mentioned method, the decomposition inhibitor may be triethylamine.

In the above-mentioned method, the decomposition of the derivative to be obtained can be suppressed with triethylamine as the decomposition inhibitor of the derivative.

(7) In the above-mentioned method, the Cookson-type derivatization reagent may be a stable isotope-labelled compound.

In the above-mentioned method, even when the Cookson-type derivatization reagent is the stable isotope-labelled compound, the decomposition of the derivative to be obtained can be suppressed. Further, derivatization with the stable isotope-labelled compound improves the selectivity of analysis with a mass spectrometer.

(8) According to one embodiment of the present invention, there is provided a derivatization reagent kit to derivatize an s-cis-diene compound with a Cookson-type derivatization reagent, the derivatization reagent kit including: a Cookson-type derivatization reagent; a reaction stopping agent to stop a derivatization reaction of the s-cis-diene compound; and a decomposition inhibitor to inhibit decomposition of a derivative to be obtained.

In the above-mentioned derivatization reagent kit, there can be provided a reagent kit in which the decomposition of the derivative to be obtained is suppressed and which is capable of accurate quantitative analysis.

(9) According to one embodiment of the present invention, there is provided a method for analyzing an s-cis-diene compound, including analyzing a derivative obtained by the above-mentioned method with a mass spectrometer.

In the above-mentioned method for analyzing an s-cis-diene compound, the derivative obtained by the above-mentioned method is analyzed with the mass spectrometer, and accurate quantitative analysis can be performed.

Preferred embodiments of the present invention are described in detail below with reference to the drawings. The following embodiments do not unduly limit the present invention as stated in the claims. In addition, all of the elements described below should not necessarily be taken as essential elements of the present invention.

1. Method for Derivatizing an s-cis-diene Compound, Derivatization Reagent Kit, and Method for Analyzing an s-cis-diene Compound 1.1 Method for Derivatizing First, a method for derivatizing according to one embodiment of the present invention is described. The method according to this embodiment is a method for derivatizing an s-cis-diene compound with a Cookson-type derivatization reagent, the method including adding, in a reaction stopping step of stopping a derivatization reaction of the s-cis-diene compound, a decomposition inhibitor to inhibit decomposition of a derivative to be obtained.

Regarding the derivative obtained by the method according to this embodiment, the oxidant remaining after being used for producing the Cookson-type derivatization reagent is decomposed by adding the decomposition inhibitor in the reaction stopping step. With this, the decomposition of the derivative to be obtained is inhibited, with the result that the derivative is obtained in high yield, and moreover, decomposed products and the like generated due to the influence of the remaining oxidant are reduced. By analyzing the derivative obtained by the method according to this embodiment with MS, in particular, LC/MS/MS using electrospray ionization (ESI) (hereinafter sometimes referred to as "LC/ESI-MS/MS), accurate quantitative analysis can be performed with high sensitivity and selectivity.

The term "derivative" as used herein refers to a compound that is formed by adding the Cookson-type derivatization reagent to an s-cis-diene moiety of the s-cis-diene compound. Further, the term "derivatization" as used herein means adding the Cookson-type derivatization reagent to the s-cis-diene compound to form a derivative. Further, the term "derivatization reaction" as used herein refers to a reaction for causing the Cookson-type derivatization reagent to react with the s-cis-diene compound to form a derivative. Further, the term "reaction stopping step" as used herein refers to a step of stopping the derivatization reaction by adding the reaction stopping agent to a reaction solution in which the derivatization reaction is being performed.

1.1.1. s-cis-diene Compound

A compound to be derivatized by the method according to this embodiment is an s-cis-diene compound. There is no particular limitation on the s-cis-diene compound, and there are given, for example, a steroid, vitamin D or vitamin D metabolites, and the like. Those s-cis-diene compounds quantitatively react with the Cookson-type derivatization reagent described later by a Diels-Alder reaction to be derivatized, and can be subjected to quantitative analysis with high sensitivity and high selectivity, in particular, in the analysis with LC-ESI-MS/MS.

Of the s-cis-diene compounds, the steroid is not particularly limited, and may be a synthetic compound or an analogue thereof without being limited to a naturally-occurring compound. There are given, for example, 7-dehydrocholesterol, ergosterol, conjugated linoleic acid, and vitamin A.

Of the s-cis-diene compounds, vitamin D belongs to secosteroid in broad classification, and is a collective term of vitamin $D_2$ derived from vegetable food and vitamin $D_3$ derived from animal food and skin production. Both vitamin $D_2$ and vitamin $D_3$ are homologues that differ only in side chain structure, and are considered to be similarly metabolized inside of a human body and to have equivalent bioactivity. Therefore, in this specification, vitamin $D_2$ and vitamin $D_3$ are not distinguished from each other and simply referred to as vitamin D. Further, in this specification, vitamin D and vitamin D metabolites are simply referred to as vitamin D, and vitamin D in this case refers to naturally-occurring or synthesized vitamin D or any one of molecular species related to vitamin D generated through transformation of vitamin D, such as intermediates and products of vitamin D metabolism.

Such molecular species of vitamin D is not particularly limited, and examples thereof include 25-hydroxy vitamin $D_3$ (25(OH)$D_3$), 25-hydroxy vitamin $D_2$ (25(OH)$D_2$), 1α,25-dihydroxy vitamin $D_3$ (1,25(OH)$_2D_3$), 23,25-dihydroxy vitamin $D_3$ (23,25(OH)$_2D_3$), 25,26-dihydroxy vitamin $D_3$ (25,26(OH)$_2D_3$), 24,25-dihydroxy vitamin $D_3$ (24,25(OH)$_2D_3$), and 4β,25-dihydroxy vitamin $D_3$ (4β,25(OH)$_2D_3$). The molecular species of vitamin D may be an isomer of the above-mentioned molecular species, and an example thereof is 3-epi-25-hydroxy vitamin $D_3$ (3-epi-25(OH)$D_3$). In addition, those molecular species of vitamin D may be sulfates, and an example thereof is 25-hydroxy vitamin $D_3$-3β-sulfate (25(OH)$D_3$S). In the quantitative analysis of vitamin D, a plurality of those molecular species of vitamin D may be contained.

1.1.2. Cookson-type Derivatization Reagent

In the method according to this embodiment, the above-mentioned s-cis-diene compound is derivatized with the Cookson-type derivatization reagent. The Cookson-type derivatization reagent selectively reacts with s-cis-diene of the compound to quantitatively form a derivative through the Diels-Alder reaction.

As such Cookson-type derivatization reagent, known and commercially available Cookson-type derivatization reagents may be used. The Cookson-type derivatization reagent is not particularly limited, and examples thereof include 4-phenyl-1,2,4-triazoline-3,5-dione (PTAD), 4-[2-(6,7-dimethoxy-4-methyl-3-oxo-3,4-dihydroquinoxalyl) ethyl]-1,2,4-triazoline-3,5-dione (DMEQTAD), 4-(4-nitrophenyl)-1,2,4-triazoline-3,5-dione (NPTAD), 4-ferrocenylmethyl-1,2,4-triazoline-3,5-dione (FMTAD), and 4-(4'-dimethylaminophenyl)-1,2,4-triazoline-3,5-dione (DAPTAD). Those Cookson-type derivatization reagents may be used alone or as a mixture thereof. Among them, from the viewpoints of sensitivity, selectivity, and stability, DAPTAD is preferably used as the Cookson-type derivatization reagent.

In this embodiment, the Cookson-type derivatization reagent may a stable isotope-labelled compound. By using a stable isotope-labelled compound as the Cookson-type derivatization reagent, the selectivity in analyzing of the derivative to be obtained with a mass spectrometer is improved. In particular, as the range of selection of transition is enlarged in the SRM mode with LC/ESI-MS/MS, a larger number of specimens and items can be simultaneously analyzed. Stable isotope for labelling include deuterium (D), carbon 13 ($^{13}C$), and nitrogen 15 ($^{15}N$). Further, the stable isotope-labelled compounds may be used alone or in combination thereof. Further, the stable isotope-labelled compound may be used simultaneously with the Cookson-type derivatization reagent that is not labelled with a stable isotope.

1.1.3. Decomposition Inhibitor

In the method for derivatizing according to this embodiment, as the decomposition inhibitor to be used for inhibiting the decomposition of the derivative to be obtained, any compound may be used without particular limitation as long as the compound volatizes easily, has no effects on separation in LC and ionization with ESI in the analysis with LC/ESI-MS/MS.

As the decomposition inhibitor that may be used in this embodiment, there are given, for example, ammonia and an amine. Any one of a primary amine, a secondary amine, and a tertiary amine may be used as the amine. Among these, ammonia, trimethylamine, triethylamine, dimethylamine, methylamine, diethylamine, or ethylamine is particularly used in terms of inhibiting the decomposition of the derivative.

1.1.4. Derivatization with Cookson-type Derivatization Reagent

In the method for derivatizing according to this embodiment, the s-cis-diene compound is derivatized with the Cookson-type derivatization reagent as described below. For example, a predetermined amount of the s-cis-diene compound is transferred to a stoppered centrifugal sedimentation tube made of glass, and a solvent is evaporated under an $N_2$ stream. Then, a predetermined amount of a Cookson-type derivatization reagent solution with a predetermined concentration is added to the resultant to cause a reaction.

Then, in the reaction stopping step of stopping the derivatization reaction of the s-cis-diene compound, for example, in the derivatization reaction is stopped by adding a reaction stopping agent solution containing an alcohol, for example, ethanol, the above-mentioned decomposition inhibitor is added to a reaction solution of the s-cis-diene compound and the Cookson-type derivatization reagent. The decomposition inhibitor exhibits an effect of inhibiting the decomposition of the derivative to be obtained as long as the decomposition inhibitor is contained in the reaction solution in the reaction stopping step. Therefore, the decomposition inhibitor may be added to the reaction solution before the reaction stopping step or may be added to the reaction stopping agent solution.

1.2. Derivatization Reagent Kit

Next, a derivatization reagent kit according to one embodiment of the present invention is described. The derivatization reagent kit according to this embodiment is a derivatization reagent kit to derivatize an s-cis-diene compound with a Cookson-type derivatization reagent, the derivatization reagent kit including: a Cookson-type derivatization reagent; a reaction stopping agent to stop a derivatization reaction of the s-cis-diene compound; and a decomposition inhibitor to inhibit decomposition of a derivative to be obtained.

Since the derivatization reagent kit includes the decomposition inhibitor, derivatization of the s-cis-diene compound with the derivatization reagent kit enables to suppress the decomposition of the derivative to be obtained the derivative is obtained in high yield, and moreover, decomposed products and the like generated in association with the decomposition are reduced. Therefore, derivatization of the s-cis-diene compound with the kit according to this embodiment enables to perform accurate quantitative analysis of the s-cis-diene compound with LC/ESI-MS/MS in particular.

In the derivatization reagent kit according to this embodiment, the Cookson-type derivatization reagent, the reaction stopping agent to stop the derivatization reaction of the s-cis-diene compound, and the decomposition inhibitor to inhibit the decomposition of the derivative to be obtained may be stored in separate containers in the form of solutions, respectively. Further, the reaction stopping agent and the decomposition inhibitor may be stored in the same container in the form of a solution.

1.3. Method for Analyzing an s-cis-Diene Compound

Next, a method for analyzing an s-cis-diene compound according to one embodiment of the present invention is described. The method for an s-cis-diene compound according to this embodiment includes analyzing a derivative obtained by the method according to the above-mentioned embodiment with a mass spectrometer.

In the method for analyzing an s-cis-diene compound according to this embodiment, the derivative obtained by the derivatization method according to this embodiment is analyzed with the mass spectrometer. Therefore, accurate quantitative analysis can be performed with high sensitivity and high selectivity.

The method for analyzing an s-cis-diene compound according to this embodiment is performed, for example, as described below.

First, the s-cis-diene compound is derivatized with the Cookson-type derivatization reagent with the kit according to this embodiment. Then, in the reaction stopping step of stopping the derivatization reaction of the s-cis-diene compound, the decomposition inhibitor to inhibit the decomposition of the derivative to be obtained is added to a reaction solution.

A part of the resultant solution containing the derivative of the s-cis-diene compound is directly subjected to, for example, LC/ESI-MS/MS. Alternatively, a solvent is evaporated from the resultant solution with an $N_2$ gas stream or the like, and a part of the resultant residue dissolved in a mobile phase for LC is subjected to, for example, LC/ESI-MS/MS.

Regarding the s-cis-diene compound to be analyzed, in the case of a biological sample other than a standard product, it is preferred to subject the sample to an extraction operation, such as solid-phase extraction and liquid-liquid extraction, before derivatization, to thereby extract and roughly purify the s-cis-diene compound. These operation enable to perform more accurate quantitative analysis with LC-ESI-MS/MS.

In the quantitative analysis with LC/ESI-MS/MS, the s-cis-diene compound is analyzed with the SRM mode by appropriately selecting transition. Measurement conditions, such as a column and mobile phase for LC to be used are appropriately selected in accordance with an analysis target and a device to be used. Further, the ionization method is preferably the above-mentioned ESI and APCI, but other ionization method such as fast atom bombardment (FAB) or the like may be used. Further, the mass spectrometer is preferably an MS/MS, but analysis can be performed even with one MS.

2. Examples

The present invention is specifically described by way of Experimental Examples and Comparative Examples. However, the present invention is by no means limited to only these Examples. In the description of the following Examples and the like, "%" means "mass %" unless otherwise specified.

In the following Examples, as an example of the method for derivatizing the s-cis-diene compound with the Cookson-type derivatization agent, description is given of an example of derivatization of vitamin D with 4-(4'-dimethylaminophenyl)-1,2,4-triazoline-3,5-dione (DAPTAD). In the following Example, triethylamine is used as the decomposition inhibitor.

2.1. Synthesis of DAPTAD (1)

DAPTAD (1) was synthesized based on the following scheme.

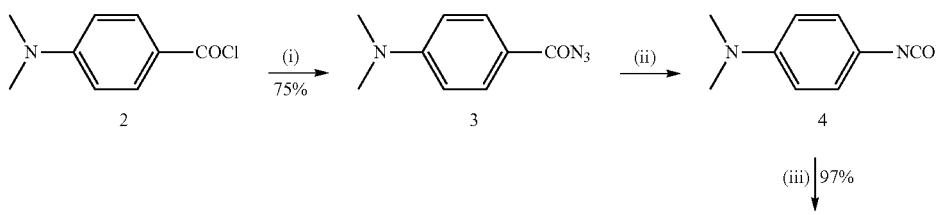

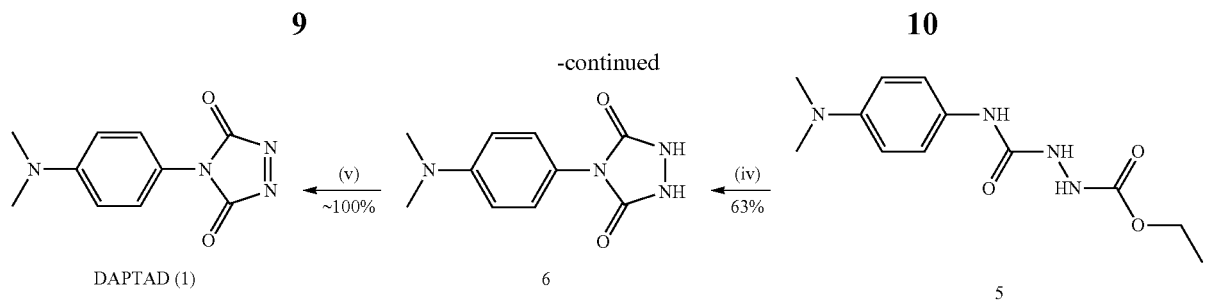

DAPTAD (1)

2.1.1. Synthesis of 4-Dimethylamino Benzoyl Azide (3) [Step (i)]

Commercially available 4-(dimethylamino)benzoyl chloride (2; 200 mg, 1.1 mmol) was added to a 30 ml recovery flask and dissolved with 15 ml of acetone. The resultant solution was ice-cooled, and 0.5 ml of an aqueous solution of sodium azide (100 mg, 1.5 mmol) was dropped to the solution. This solution was stirred for 1 hour on ice bath under atmospheric pressure. The resultant reaction solution was diluted with 25 ml of ethyl acetate, and washed with 25 ml of saturated saline three times (25 ml×3). An organic layer was dried over magnesium sulfate, and then a solvent was evaporated under reduced pressure. After that, a residue was chromatographed on a silica gel column ("Silicagel 60 (63-200 µm), Merck Ltd.,", 150×120 mm i.d.). An elution fraction of hexane-ethyl acetate (4:1, v/v) was collected, and a solvent was evaporated under reduced pressure, to thereby provide 4-dimethylamino benzoyl azide (3) as a colorless solid (157 mg, 76%, 0.8 mmol).

2.1.2. Synthesis of 1-Ethoxycarbonyl-4-(4'-dimethylaminophenyl)semicarbazide (5) [Steps (ii) and (iii)]

The obtained 4-dimethylamino benzoyl azide (3) (157 mg, 76%, 0.8 mmol) was transferred to a 30 ml recovery flask, dissolved with 5 ml of toluene, and refluxed for 20 minutes under atmospheric pressure, thereby being converted into a compound (4) [Step (ii)]. 5 ml of a benzene solution of ethyl carbazate (100 mg, 1.0 mmol) was added to the reaction solution without the compound (4) being isolated, and the mixture was stirred at room temperature for 1 hour under atmospheric pressure. After that, the resultant was refluxed for 1 hour. The resultant reaction solution was allowed to cool, and then a generated precipitate was subjected to suction filtration, to thereby provide 1-ethoxycarbonyl-4-(4'-dimethylaminophenyl)semicarbazide (5) as a colorless solid (213 mg, 97%) [Step (iii)]. The obtained 1-ethoxycarbonyl-4-(4'-dimethylaminophenyl)semicarbazide (5) was used in a next reaction without purification.

2.1.3. Synthesis of 4-(4'-Dimethylaminophenyl)-1,2,4-triazolidine-3,5-dione (6) [Step (iv)]

The obtained 1-ethoxycarbonyl-4-(4'-dimethylaminophenyl)semicarbazide (5) was transferred to a 30 ml recovery flask. 10 ml of an aqueous solution of potassium carbonate (100 mg, 0.7 mmol) was added to the 30 ml recovery flask, and the mixture was stirred at 90° C. for 3 hours under atmospheric pressure. Acetic acid was added to the reaction solution while checking the reaction solution with universal pH test paper to adjust the pH of the reaction solution to about 6. A solvent was evaporated under reduced pressure, and the resultant was chromatographed on ODS column ("Wakogel™100C18 (63-212 µm), Wako Pure Chemical Industries, Ltd.,", 300×10 mm i.d.). Potassium acetate and the like were removed with 50 ml of water ($H_2O$). Then, a methanol (MeOH)-water (1:1, v/v) elution fraction was collected, and a solvent was evaporated under reduced pressure. After that, the resultant was recrystallized with water to provide a brown amorphous crystal (52.4 mg, 63%) of 4-(4'-dimethylaminophenyl)-1,2,4-triazolidine-3,5-dione (6).

2.1.4. Synthesis of 4-(4'-Dimethylaminophenyl)-1,2,4-triazoline-3,5-dione (DAPTAD:1) [Step (v)]

The obtained 4-(4'-dimethylaminophenyl)-1,2,4-triazolidine-3,5-dione (6; 4 mg, 9.1 µmol) was transferred to a 10 ml test tube with a lid, and 10 ml of ethyl acetate was added to the test tube to suspend 4-(4'-dimethylaminophenyl)-1,2, 4-triazolidine-3,5-dione. Iodobenzene diacetate (6 mg, 9.3 µmol) was added to the suspension, and the resultant was stirred at room temperature for 3 hours under atmospheric pressure. The reaction solution was subjected to centrifugation (1,000 g, 10 minutes), and a supernatant was stored as the DAPTAD ethyl acetate solution (4 µg/10 µl) (1) at −18° C. This DAPTAD solution was used directly for derivatization of vitamin D.

2.2. LC/ESI-MS/MS Measurement of DAPTAD-V.D.

2.2.1 DAPTAD-Derivatization of V.D.

A standard product of a vitamin $D_3$ metabolite [25(OH)$D_3$ or 25(OH)$D_3$S] was transferred to a 10 ml stoppered centrifugal sedimentation tube made of glass, and a solvent was evaporated under an $N_2$ gas stream. The DAPTAD ethyl acetate solution (4 µg/10 µl; 50 µl) obtained in the section 2.1. was added to the resultant, and the mixture was left at room temperature for 1 hour. Then, 40 µl of ethanol containing 0.1% triethylamine was added to the resultant to stop the reaction. A solvent was evaporated under an $N_2$ gas stream. After that, a residue was dissolved in 100 µl of a mobile phase, and a part (10 µl) of the resultant solution was subjected to LC/ESI-MS/MS. In Comparative Examples, 40 µl of ethanol without trimethylamine was added to stop the reaction.

2.2.2. Device for Use

A Waters (trademark) Quattro Premier XE triple quadrupole mass spectrometer (Nihon Waters K.K.) connected to an LC-e2695 chromatograph (Nihon Waters K.K.) was used as LC/MS/MS, and ESI was used for the ionization method. Analysis was performed under the following analysis conditions.

2.2.3. Analysis Conditions

Analysis target: 25(OH)$D_3$-DAPTAD and 25(OH)$D_3$S-DAPTAD

Column: YMC-Pack Pro C18 RS (3 µm, 150×2.0 mm i.d.)

Column temperature: 40° C.

Mobile phase: 0.05% formic acid-containing methanol-10 mM ammonium formate (4:1, v/v)

Flow rate: 0.2 ml/min

Ionization mode: ESI (+)

Capillary voltage: 2.80 kV

Cone voltage: 40 V [25(OH)$D_3$-DAPTAD], 35 V [25 (OHD)$_3$S-DAPTAD], or 30 V [25(OH)$D_3$-DAPTAD]

CE: 25 eV

Source temperature: 120° C.
Desolvation temperature: 350° C.
Desolvation gas ($N_2$) flow rate: 600 L/h
Cone gas ($N_2$) flow rate: 50 L/h
Collision gas (Ar) flow rate: 0.19 ml/min
SRM transition:
m/z 619.6→m/z 341.3 [25(OH)$D_3$-DAPTAD]
m/z 558.4→m/z 298.0 [25(OH)$D_3$-PTAD]
m/z 699.6→m/z 421.2 [25(OH)$D_3$S-DAPTAD]

For analysis of data, QuanLynx that was an automatic processing system in Waters (trademark) MassLynx 4.1 software was used.

2.2.4. Analysis Results

Figure 2:
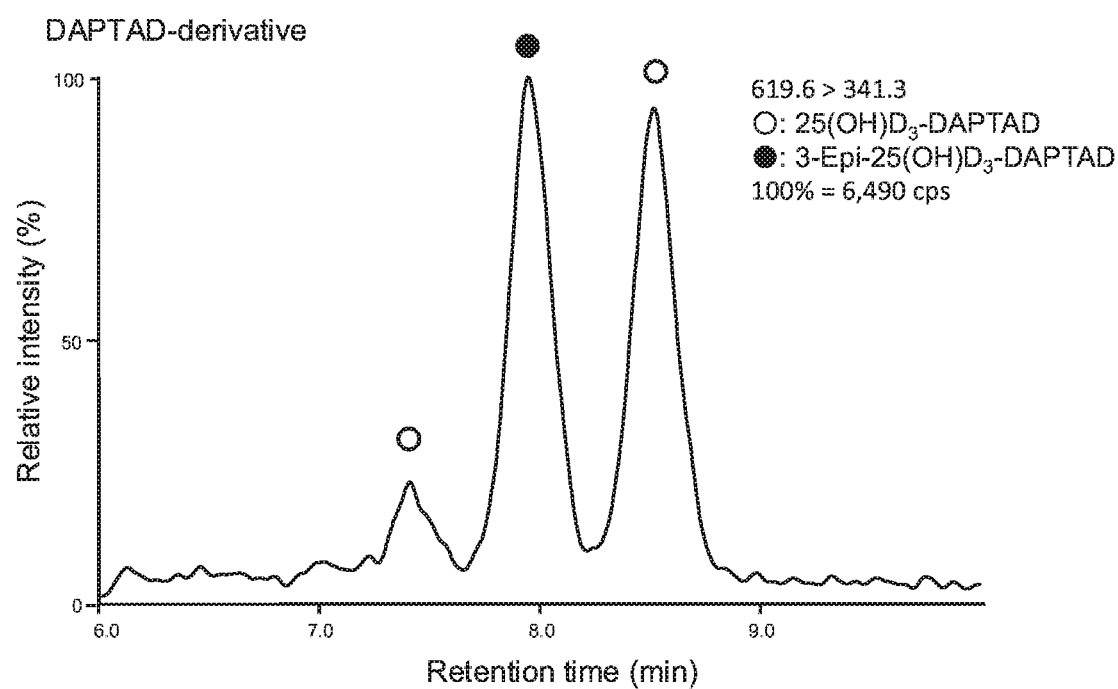
FIG. 2 is a mass chromatogram of $25(OH)D_3$ and 3-epi-$25(OH)D_3$ derivatized with DAPTAD.

First, as shown in FIG. 1 to FIG. 4, DAPTAD-derivatives are more sensitive and selective than PTAD-derivatives. FIG. 1 is a mass chromatogram of 25(OH)$D_3$ and 3-epi-25(OH)$D_3$ derivatized with PTAD that adjusted to the same amount (amount equivalent to 2 pg per injection). FIG. 2 is a mass chromatogram of 25(OH)$D_3$ and 3-epi-25(OH)$D_3$ derivatized with DAPTAD that adjusted to the same amount (amount equivalent to 2 pg per injection). As shown in FIG. 1, while the peaks of the 25(OH)$D_3$-PTAD and 3-epi-25(OH)$D_3$-PTAD were not separated, as shown in FIG. 2, the peaks of the 25(OH)$D_3$-DAPTAD and 3-epi-25(OH)$D_3$-DAPTAD were clearly separated and the selectivity was improved.

Besides PTAD and DAPTAD, the Cookson-type reagents attack both α and β sides of vitamin D metabolites to generate an epimer at the C-6-position. For this reason, there are two peaks of a 6R-isomer (eluted first in chromatography) and a 6S-isomer (major product that is eluted later in chromatography) as the peaks of 25(OH)$D_3$. In 3-epi-25(OH)$D_3$, the 6R-isomer and the 6S-isomer were coeluted without being separated, and the peaks of the derivatives were observed as one peak. Further, comparing the relative intensities of FIG. 1 and FIG. 2, the DAPTAD-derivative shown in FIG. 2 had high relative intensity of 6,490 cps.

Figure 3:
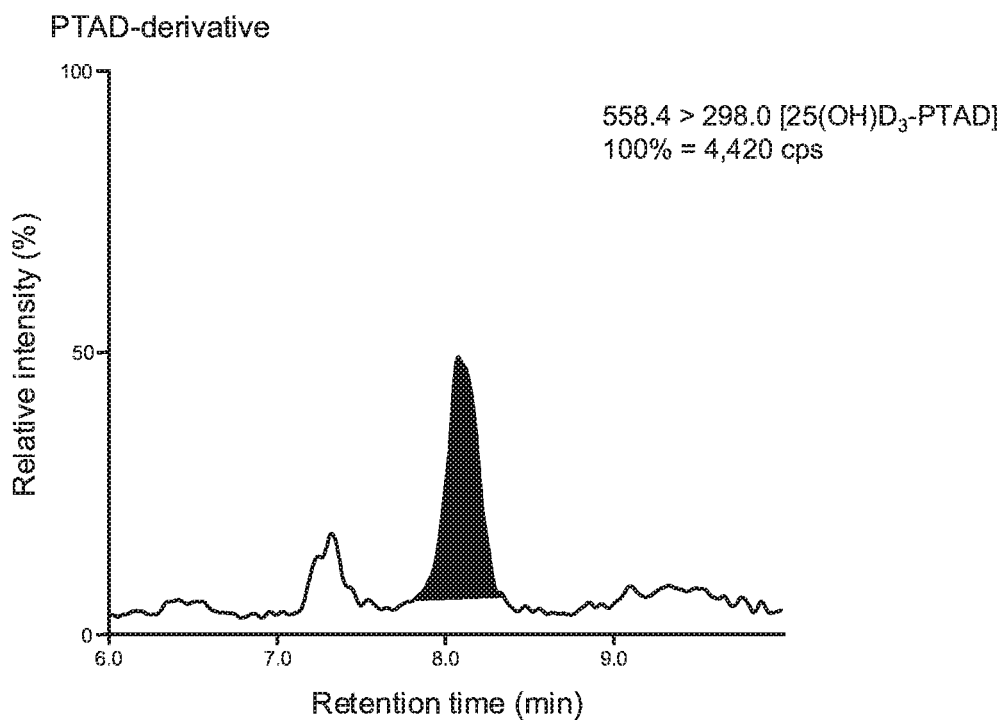
FIG. 3 is a mass chromatogram of $25(OH)D_3$-PTAD.
Figure 4:
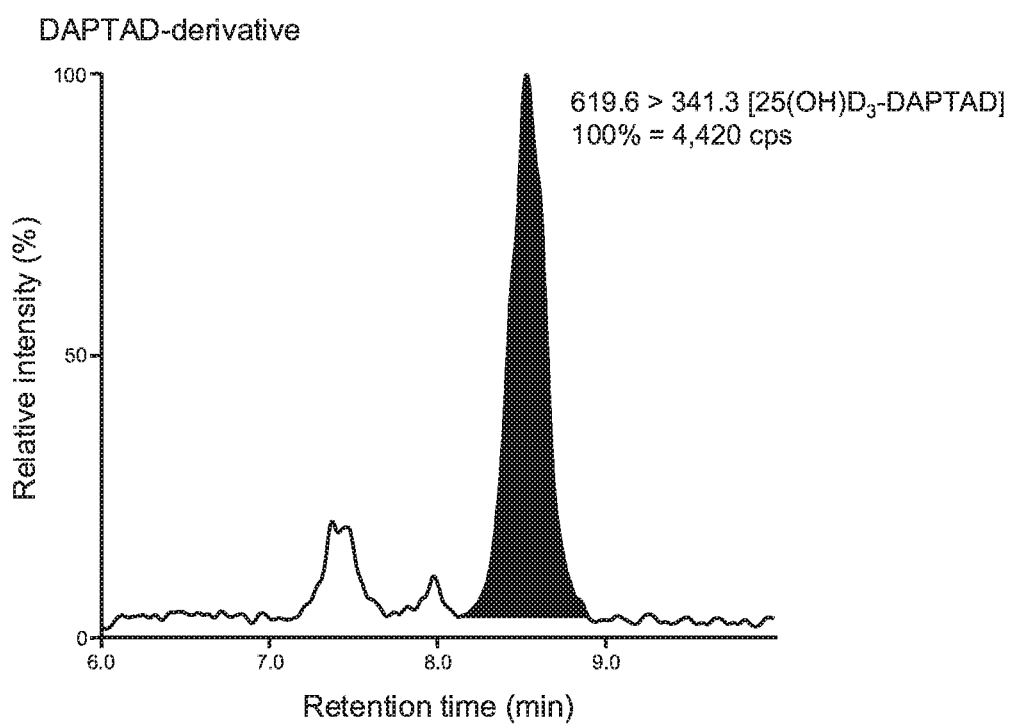
FIG. 4 is a mass chromatogram of $25(OH)D_3$-DAPTAD.

Examples of the above-mentioned results described based on the DAPTAD-derivative relative intensity are shown in FIG. 3 and FIG. 4. FIG. 3 is a mass chromatogram of 25(OH)$D_3$-PTAD, and FIG. 4 is a mass chromatogram of 25(OH)$D_3$-DAPTAD. Comparing the relative intensities of FIG. 3 and FIG. 4, the relative intensity of FIG. 4 is higher than relative intensity of FIG. 3 and the effect of the DAPTAD-derivatization was observed.

Next, FIG. 5 to FIG. 12 are each a graph for showing the effect of the method for derivatizing according to this embodiment.

First, description is given of the effect of adding triethylamine as the decomposition inhibitor in the reaction stopping step of derivatizing 25(OH)$D_3$ with DAPTAD as shown in FIG. 5 to FIG. 8.

Figure 5:
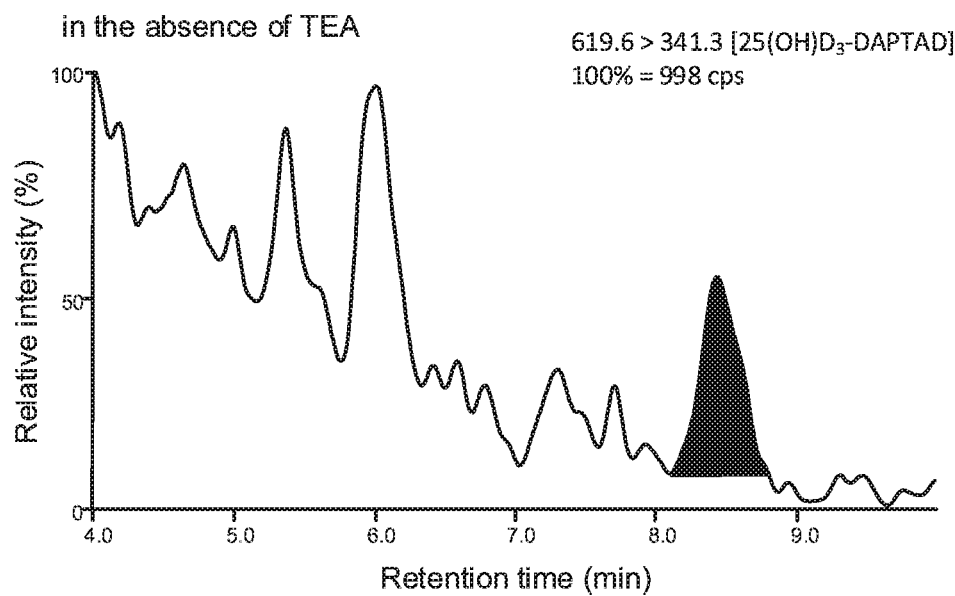
FIG. 5 is a mass chromatogram of Comparative Example 1.
Figure 6:
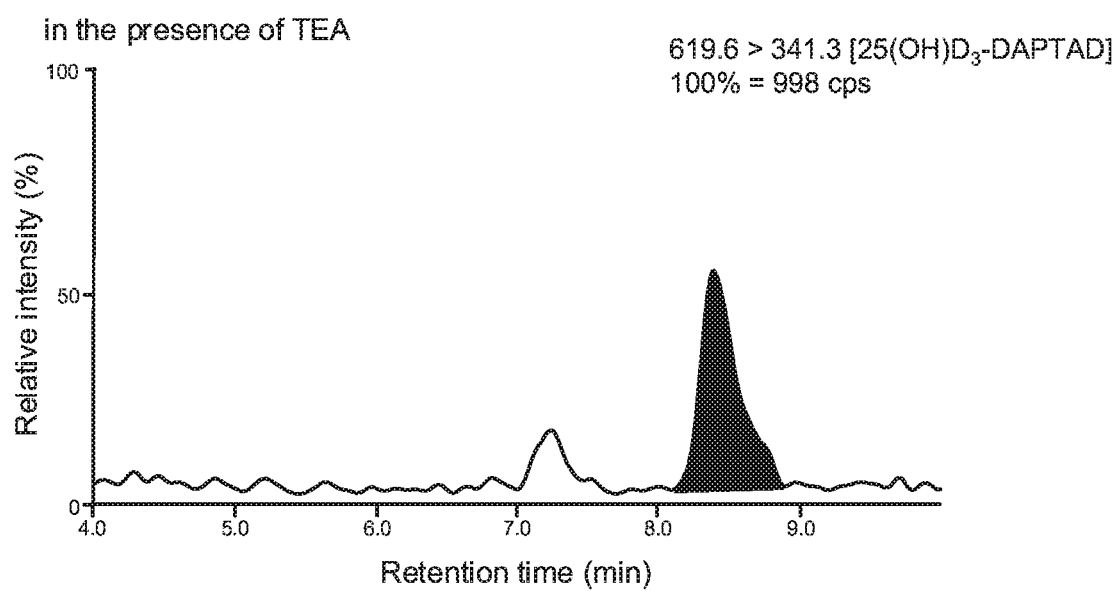
FIG. 6 is a mass chromatogram of Example 1.
Figure 7:
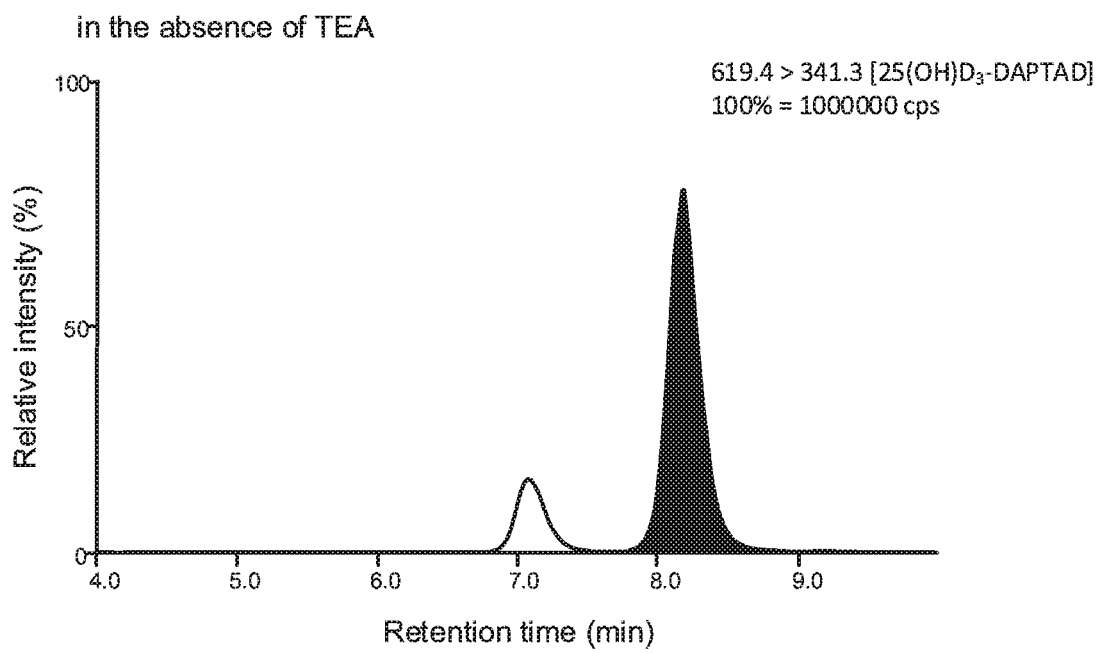
FIG. 7 is a mass chromatogram of Comparative Example 2.
Figure 8:
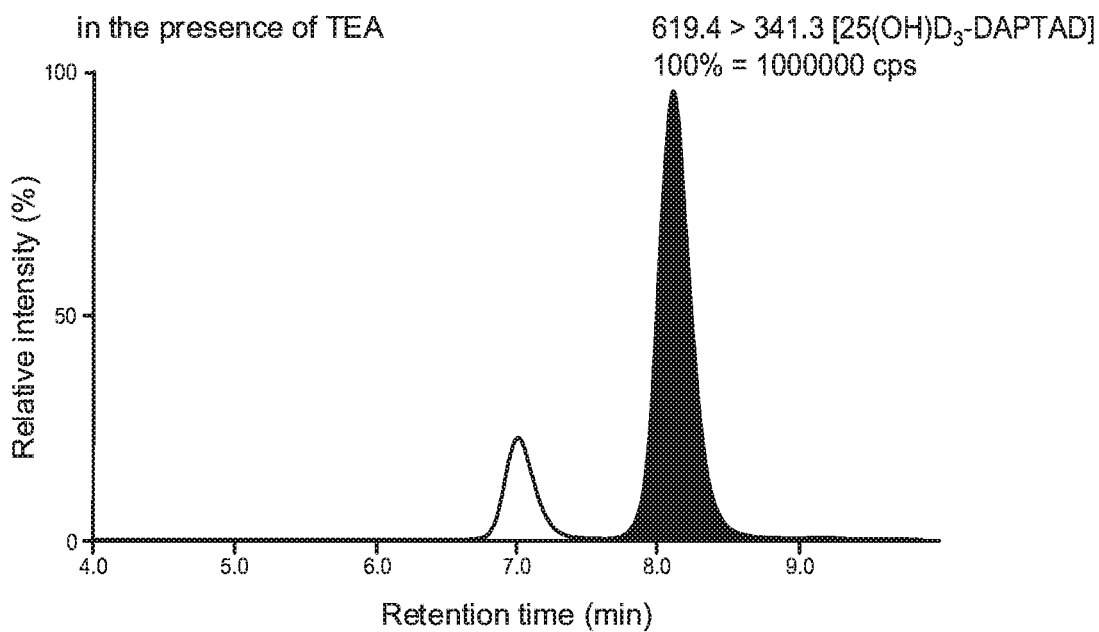
FIG. 8 is a mass chromatogram of Example 2.

FIG. 5 and FIG. 7 are mass chromatograms of examples (Comparative Examples 1 and 2) in the absence of triethylamine as the decomposition inhibitor in the reaction stopping step of stopping the derivatization of 25(OH)$D_3$ with DAPTAD. FIG. 6 and FIG. 8 are mass chromatograms of examples (Examples 1 and 2) in the presence of triethylamine as the decomposition inhibitor in the reaction stopping step of stopping the derivatization of 25(OH)$D_3$ with DAPTAD. In Examples 1 and 2 and Comparative Examples 1 and 2, compounds other than 25(OH)$D_3$ are absence in the sample to be derivatized the analysis conditions are the same as above, and the observed transition is 25(OH)$D_3$-DAPTAD. Further, in FIG. 5 and FIG. 6, the sample equivalent to 2.5 pg was injected. In FIG. 7 and FIG. 8, the sample equivalent to 100 pg was injected.

First, comparing FIG. 5 and FIG. 6 (Comparative Example 1 and Example 1) in which the sample equivalent to 2.5 pg was injected, noise in the transition of 25(OH)$D_3$-DAPTAD in SRM measurement was reduced and a signal-to-noise-ratio (S/N ratio) was increased in FIG. 6 (Example 1) as compared to FIG. 5 (Comparative Example 1). This is considered the addition of triethylamine as the decomposition inhibitor in the derivatizing 25(OH)$D_3$ with DAPTAD suppress the decomposition of a 25(OH)$D_3$-DAPTAD and reduce the noise.

Further, comparing FIG. 7 and FIG. 8 (Comparative Example 2 and Example 2), in which the sample equivalent to 100 pg was injected, the relative intensity of the derivative was significantly reduced as compared to noise in FIG. 7 (Comparative Example 2). However, the relative intensity in the transition of 25(OH)$D_3$-DAPTAD in SRM measurement was increased in FIG. 8 (Example 2) as compared to FIG. 7 (Comparative Example 2).

As described above, the effect of inhibition the decomposition of 25(OH)$D_3$-DAPTAD was obtained by adding triethylamine as the decomposition inhibitor in the reaction stopping step of stopping the derivatization of 25(OH)$D_3$ with DAPTAD.

Next, description is given of the effect of adding triethylamine as the decomposition inhibitor in the reaction stopping step of derivatizing 25(OH)$D_3$S with DAPTAD as shown in FIG. 9 to FIG. 12.

Figure 9:
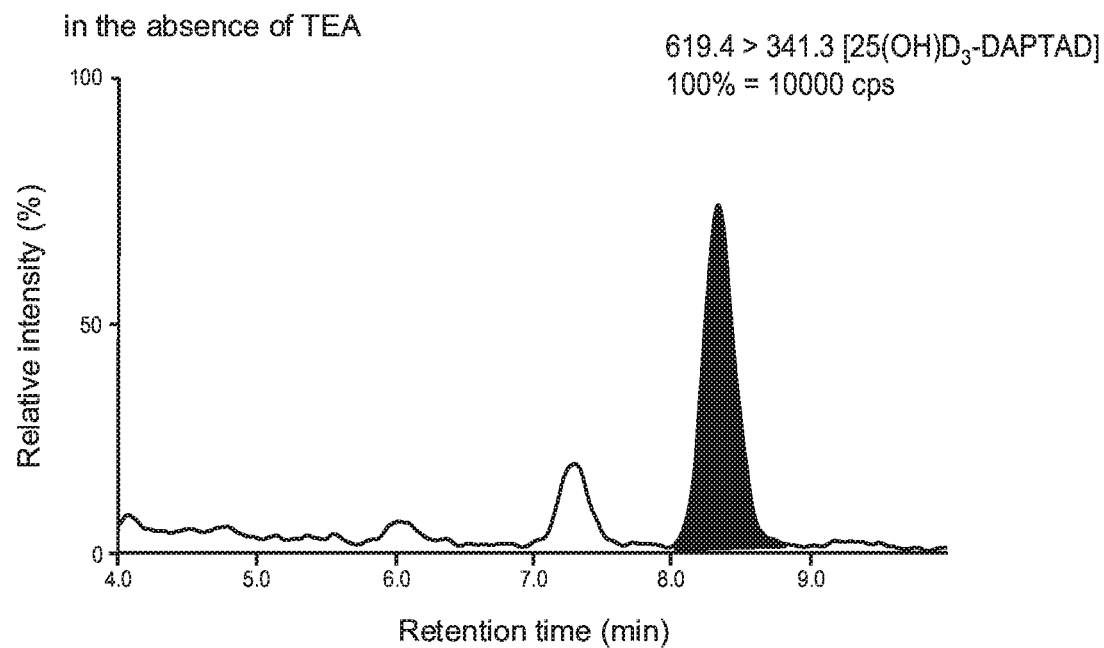
FIG. 9 is a mass chromatogram of Comparative Example 3.
Figure 10:
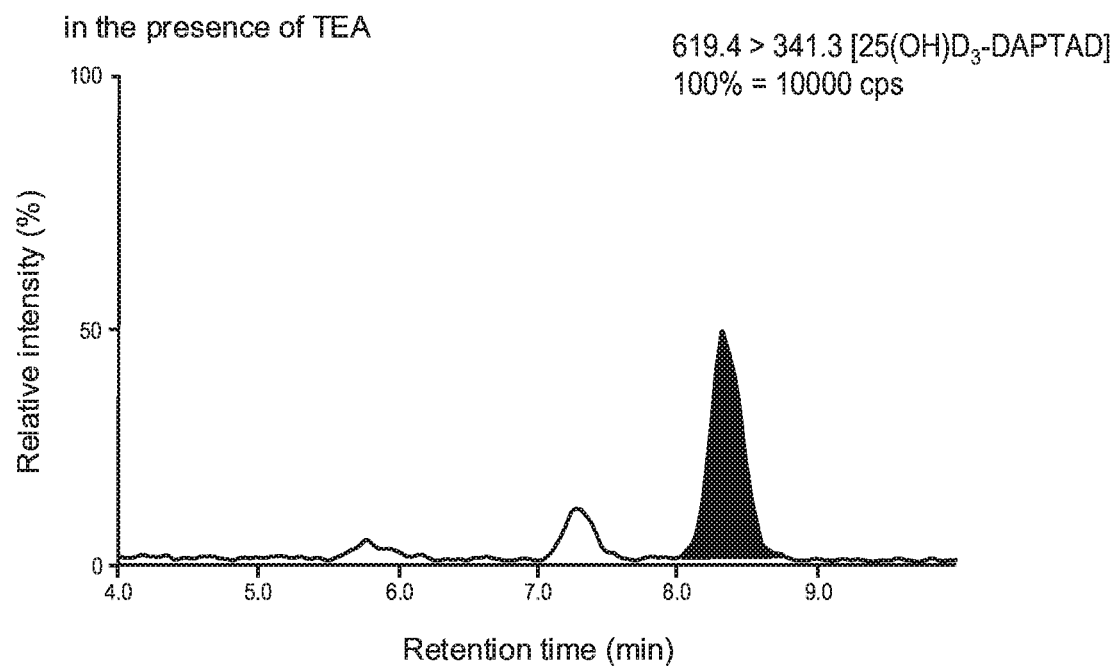
FIG. 10 is a mass chromatogram of Example 3.
Figure 11:
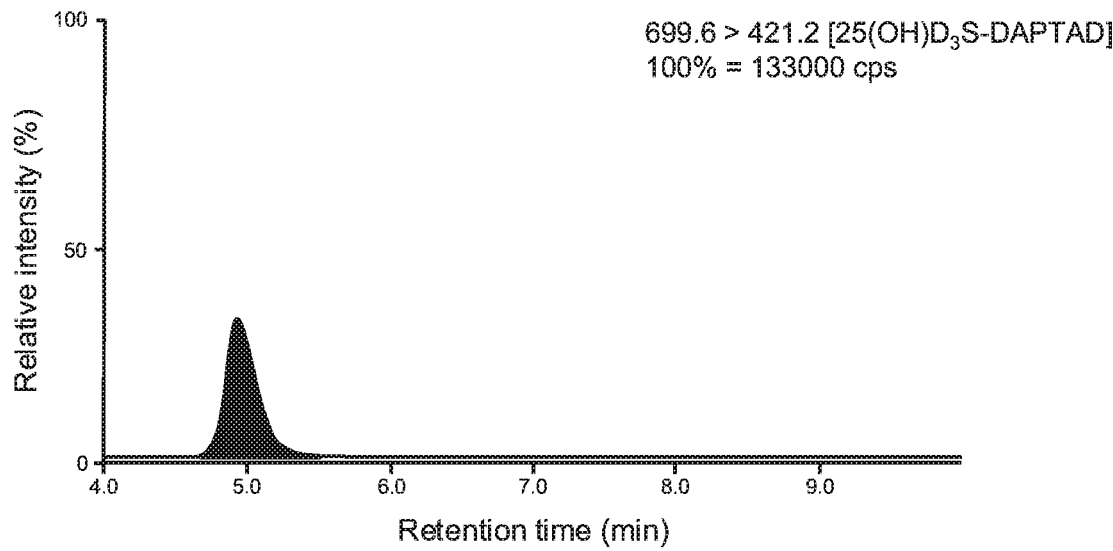
FIG. 11 is a mass chromatogram of Comparative Example 4.
Figure 12:
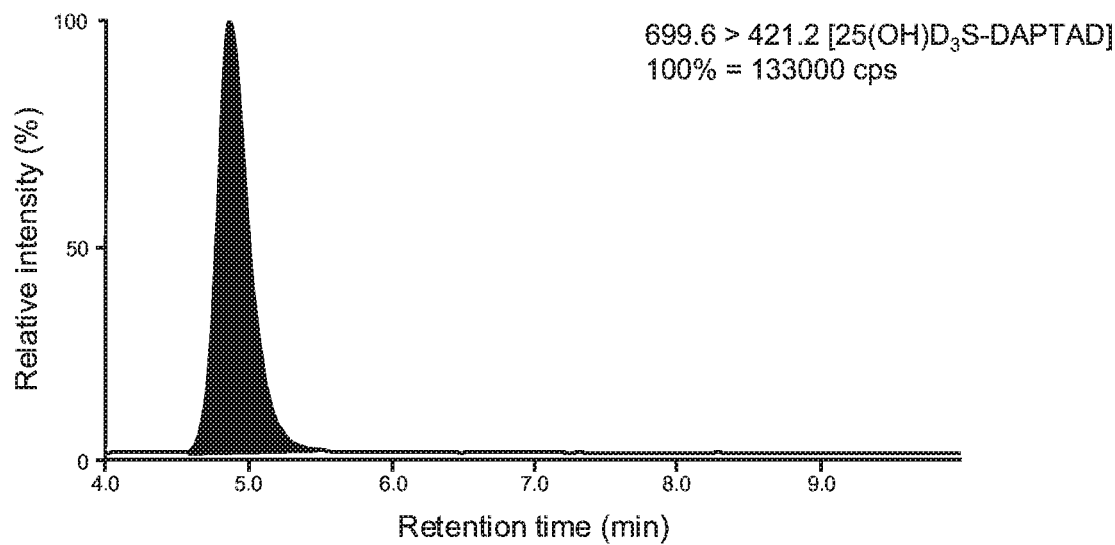
FIG. 12 is a mass chromatogram of Example 4.

FIG. 9 and FIG. 11 are mass chromatograms of examples (Comparative Examples 3 and 4) in the absence of triethylamine as the decomposition inhibitor in the reaction stopping step of stopping the derivatization of 25(OH)$D_3$S with DAPTAD. FIG. 10 and FIG. 12 are mass chromatograms of examples (Examples 3 and 4) in the presence of triethylamine as the decomposition inhibitor in the reaction stopping step of stopping the derivatization of 25(OH)$D_3$S with DAPTAD. In FIG. 9 and FIG. 10, the observed transition is 25(OH)$D_3$-DAPTAD. In FIG. 11 and FIG. 12, the observed transition is 25(OH)$D_3$S-DAPTAD. In Examples 3 and 4, and Comparative Examples 3 and 4, compounds other than 25(OH)$D_3$S, for example, 25(OH)$D_3$ are absence in the sample to be derivatized, and the analysis conditions are the same as above.

Comparing FIG. 9 and FIG. 10, the ion intensity of the 25(OH)$D_3$-DAPTAD peak in FIG. 9 observed during a retention time of from 8.0 minutes to 9.0 minutes was higher than FIG. 8. Meanwhile, comparing FIG. 11 and FIG. 12, the ion intensity of 25(OH)$D_3$S-DAPTAD peak in FIG. 12 observed around a retention time of 5.0 minutes was higher than FIG. 11. From these, derivatizing 25(OH)$D_3$S with DAPTAD in the absence of triethylamine, 25(OH)$D_3$S-DAPTAD may decompose to 25(OH)$D_3$-DAPTAD through desulfoconjugation, however, in the presence of triethylamine the decomposition of 25(OH)$D_3$S-DAPTAD to 25(OH)$D_3$-DAPTAD is suppressed.

Both 25(OH)$D_3$S and 25(OH)$D_3$ are endogenous vitamin D metabolites, and both of them are object to be measured. As shown in FIG. 9 and FIG. 11, decomposition of a part of the 25(OH)$D_3$S-DAPTAD to 25(OH)$D_3$-DAPTAD makes accurate quantification of 25(OH)$D_3$S-DAPTAD difficult. Meanwhile, as shown in FIG. 10 and FIG. 12, in the presence of the decomposition inhibitor in the reaction stopping step, the decomposition of 25(OH)$D_3$S-DAPTAD is suppressed, and accurate quantification of 25(OH)$D_3$S-DAPTAD is possible.

Further, as shown in the results of Examples 1 and 2 and Comparative Examples 1 and 2, in the presence of triethylamine as the decomposition inhibitor in the reaction stopping step of derivatizing 25(OH)D$_3$ with DAPTAD, the effect of inhibition the decomposition of the derivative is also obtained, the ion intensity is not reduced. Therefore, in the case of a sample in which 25(OH)D$_3$ and 25(OH)D$_3$S coexist, adding triethylamine as the decomposition inhibitor in the reaction stopping step of stopping the derivatization with DAPTAD enables to quantify each of them with high accuracy, irrespective of whether any one of 25(OH)D$_3$ and 25(OH)D$_3$S is intended to be measured or both of them are intended to be measured simultaneously and to improve reliability of a measurement value.

As a result, even if 25(OH)D$_3$-DAPTAD and 25(OH)D$_3$S-DAPTAD may be decomposed with an oxidant (iodobenzene diacetate) that remained in the preparation of DAPTAD, the presence of triethylamine as the decomposition inhibitor in the reaction stopping step of stopping the DAPTAD derivatization enables to inhibit the decomposition of the derivative. Furthermore, the presence of triethylamine enables to enhance sensitivity and accuracy in the quantitative analysis of 25(OH)D$_3$-DAPTAD and 25(OH)D$_3$S-DAPTAD than before.

The present invention is not limited to the embodiments described above, and various modifications may be made thereto. For example, the present invention includes various other configurations substantially the same as the configurations described above in connection with the embodiments (e.g., a configuration having the same function, method, and results, or a configuration having the same objective and effects). The present invention also includes a configuration in which an unsubstantial element described above in connection with the embodiments is replaced by another element. The present invention also includes a configuration having the same actions and effects as those of the configurations described above in connection with the embodiments, or a configuration capable of achieving the same objective as that of the configurations described above in connection with the embodiments. The present invention further includes a configuration in which a known technology is added to the configurations described in connection with the embodiments.

Although only some embodiments of the present invention have been described in detail above, those skilled in the art would readily appreciate that many modifications are possible in the embodiments without materially departing from the novel teachings and advantages of the present invention. Accordingly, all such modifications are intended to be included within the scope of the present invention.

What is claimed is:

1. A method for derivatizing an s-cis-diene compound with a Cookson-type derivatization reagent,
    the method comprising adding, in a reaction stopping step of stopping a derivatization reaction of the s-cis-diene compound, a decomposition inhibitor to inhibit decomposition of a derivative to be obtained, and
    evaporating solvent after completion of the reaction stopping step to form a residue of the derivatized s-cis-diene compound,
        wherein the Cookson-type derivatization reagent is 4-(4'-dimethylaminophenyl)-1,2,4-triazoline-3,5-dione (DAPTAD), the s-cis-diene compound is vitamin D or a vitamin D metabolite, and the decomposition inhibitor is trimethylamine.

2. A derivatization reagent kit to derivatize an s-cis-diene compound with a Cookson-type derivatization reagent and form a residue of the derivatized s-cis-diene compound,
    the derivatization reagent kit comprising:
    a Cookson-type derivatization reagent;
    a reaction stopping agent to stop a derivatization reaction of the s-cis-diene compound; and
    a decomposition inhibitor to inhibit decomposition of a derivative to be obtained,
    wherein the Cookson-type derivatization reagent is 4-(4'-dimethylaminophenyl)-1,2,4-triazoline-3,5-dione (DAPTAD), the s-cis-diene compound is vitamin D or a vitamin D metabolite, and the decomposition inhibitor is trimethylamine.

3. A method for analyzing an s-cis-diene compound, comprising analyzing a derivative obtained by the method of claim 1 with a mass spectrometer.

4. The method of claim 1, wherein the decomposition inhibitor is added to a derivatization reaction solution for the derivatization reaction before adding a reaction stopping agent.

5. The method of claim 1, wherein the decomposition inhibitor is added to a reaction stopping agent solution that comprises a reaction stopping agent, and then the stopping agent solution is added to a derivatization reaction solution for the derivatization reaction.

* * * * *